(12) United States Patent
Morita et al.

(10) Patent No.: US 10,241,312 B2
(45) Date of Patent: Mar. 26, 2019

(54) TOTAL INTERNAL REFLECTION MICROSCOPE

(71) Applicant: NIKON CORPORATION, Tokyo (JP)

(72) Inventors: Takayuki Morita, Fujisawa (JP);
Akitoshi Suzuki, Yokohama (JP);
Tomoko Kobayashi, Fujisawa (JP);
Keita Masuda, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 253 days.

(21) Appl. No.: 15/142,804

(22) Filed: Apr. 29, 2016

(65) Prior Publication Data

US 2016/0246043 A1 Aug. 25, 2016

Related U.S. Application Data

(63) Continuation of application No. PCT/JP2014/005474, filed on Oct. 29, 2014.

(30) Foreign Application Priority Data

Oct. 30, 2013 (JP) .................................. 2013-224859

(51) Int. Cl.
*G02B 21/06* (2006.01)
*G02B 21/16* (2006.01)
(Continued)

(52) U.S. Cl.
CPC ............ *G02B 21/06* (2013.01); *G02B 21/008* (2013.01); *G02B 21/16* (2013.01); *G02B 21/365* (2013.01);
(Continued)

(58) Field of Classification Search
CPC ................ G02B 21/002; G02B 21/008; G02B 21/0032; G02B 21/0052; G02B 21/02;
(Continued)

(56) References Cited

U.S. PATENT DOCUMENTS

| 2003/0058530 A1 | 3/2003 | Kawano |
| 2005/0207005 A1 | 9/2005 | Kawano |

(Continued)

FOREIGN PATENT DOCUMENTS

| JP | 2003-098439 A | 4/2003 |
| JP | 2004-021222 A | 1/2004 |

(Continued)

OTHER PUBLICATIONS

May 3, 2016 International Preliminary report on Patentability issued in International Patent Application No. PCT/JP2014/005474.
Feb. 3, 2015 International Search Report issued in International Patent Application No. PCT/JP2014/005474.
(Continued)

*Primary Examiner* — Mustak Choudhury
(74) *Attorney, Agent, or Firm* — Oliff PLC

(57) ABSTRACT

The total internal reflection microscope has an illumination optical system that relays light from a light source with a relay optical system, forms an image of the light source on the incident pupil plane of the objective lens and irradiates a sample with the illumination light via an objective lens, has an angle adjustment mirror for changing the position of the image of the light source in a direction orthogonal to the optical axis, an optical detector for detecting the intensity of the returning illumination light reflected by the sample and collected by the objective lens, and a controller for determining the operation amount of the angle adjustment mirror, wherein the controller determines the operation amount of the angle adjustment mirror so that the illumination light is totally reflected at the sample based on the change in intensity of the returning light when the angle adjustment mirror is changed.

21 Claims, 9 Drawing Sheets

(51) Int. Cl.
*G02B 21/36* (2006.01)
*G02B 27/56* (2006.01)
*G02B 21/00* (2006.01)
*G01N 21/64* (2006.01)

(52) U.S. Cl.
CPC ........... *G02B 27/56* (2013.01); *G01N 21/648* (2013.01); *G01N 21/6458* (2013.01)

(58) Field of Classification Search
CPC .... G02B 21/06; G02B 21/082; G02B 21/084; G02B 21/10; G02B 21/16; G02B 21/18; G02B 21/32; G02B 21/34; G02B 21/361; G02B 21/365; G02B 21/367; G02B 27/0018; G02B 27/56; G02B 23/04; G01Q 10/04; G01J 3/10; G01J 3/32; G01J 3/36; G01N 2021/212
USPC ................. 359/363, 368, 385–389; 348/79
See application file for complete search history.

(56) References Cited

U.S. PATENT DOCUMENTS

| | | | |
|---|---|---|---|
| 2010/0171946 | A1 | 7/2010 | Hecker |
| 2010/0315708 | A1* | 12/2010 | Amberger ............ G02B 21/06 359/389 |
| 2012/0002031 | A1* | 1/2012 | Pertsinidis ............ G02B 21/16 348/79 |

FOREIGN PATENT DOCUMENTS

| | | |
|---|---|---|
| JP | 2009-505126 A | 2/2009 |
| JP | 2009-98229 A | 5/2009 |
| JP | 2011-118069 A | 6/2011 |
| JP | 2011-118265 A | 6/2011 |
| JP | 2013-221960 A | 10/2013 |

OTHER PUBLICATIONS

Apr. 17, 2018 Office Action issued in Japanese Patent Application No. 2017-132570.

* cited by examiner

TOTAL INTERNAL REFLECTION MICROSCOPE

RELATED APPLICATIONS

This is a continuation of PCT International Application No. PCT/JP2014/005474, filed on Oct. 29, 2014, which is hereby incorporated by reference. This application also claims the benefit of Japanese Patent Application No. 2013-224859, filed in Japan on Oct. 30, 2013, which is hereby incorporated by reference.

TECHNICAL FIELD

The present invention relates to a total internal reflection microscope.

BACKGROUND ART

In detecting the illumination angle of a conventional total internal reflection microscope, the total reflection angle has been calculated and secured by detecting the position of the illumination light in the entrance pupil of the object lens via a CCD or a position sensitive detector (PSD) (for example, see Patent Document 1). In this case, the positional precision of the illumination light depends on the resolution of the detection element and the projection magnification of the incident pupil of the objective lens 16 relative to the detection element, and in order to improve precision, an expensive high-resolution detection element must be used, or the projection magnification must be increased and a larger detection optical system must be permitted. If the projection magnification is increased, the size of the detection element must also be made larger, leading to cost increase. Describing specifically, the position detection resolution of a general CCD or PSD is on the order of several μm to several tens of μm, and this multiplied by the reciprocal of the projection magnification of the objective lens from the incident pupil to the detection element corresponds to the collecting position detection precision of the illumination light in the incident pupil. That is, the higher the projection magnification is, the higher the position detection precision can be made.

CITATION LIST

Patent Literatures

Patent Document 1: US Patent 2010/0171946

SUMMARY OF INVENTION

Technical Problem

However, a 60× to 100× incident pupil of an objective lens used for total internal reflection microscope observation has a diameter on the order of 6 to 10 mm, and detection elements of a size that can project with a double or triple magnification are generally few and expensive. In a total internal reflection microscope, even if the difference in collecting position at the incident pupil of the objective lens is on the order of several μm, the observation image is impacted, and changes the evanescent field penetration depth. Relating thereto, it is difficult to manage and secure detection precision with a detection element that has only a resolution which is on the same order as the several μm.

With the foregoing in view, an object of the present invention is to provide a total internal reflection microscope that can control with good precision the illumination angle of a total internal reflection microscope and has a simple configuration.

Solution to Problem

In order to resolve the aforementioned problem, the total internal reflection microscope according to the present invention includes an illumination optical system for relaying light from a light source with a relay optical system and forming an image of the light source on the incident pupil of an objective lens or the vicinity thereof and irradiating a sample with the light through the objective lens, the total internal reflection microscope including an incident angle adjustment part for changing the position of the image of the light source in a direction orthogonal to the optical axis, an optical detector for detecting intensity of the returning light that is the light reflected by the sample and collected by the objective lens, and a controller for determining the operation amount of the incident angle adjustment part, wherein the controller determines the operation amount of the incident angle adjustment part based on the change in intensity of the returning light when the incident angle adjustment part is changed.

With this type of total internal reflection microscope, it is preferable to further include a focus lens for changing the position of the image of the light source in the optical axis direction, wherein the controller determines the operation amount of the incident angle adjustment part and the focus lens based on the change in intensity of the returning light when the incident angle adjustment part and the focus lens are changed.

With this type of total internal reflection microscope, it is preferable for the controller to determine the operation amount of the incident angle adjustment part so the light is totally reflected at the sample based on the change in intensity of the returning light when the incident angle adjustment part is changed, and to determine the operation amount of the focus lens so the light becomes parallel light based on the change in intensity of the returning light when the focus lens is changed.

With this type of total internal reflection microscope, the controller preferably adjusts the position of the light source image in a direction orthogonal to the optical axis direction in the incident pupil of the objective lens or the vicinity thereof so that the light is totally reflected at the sample, and adjusts the position of the light source image in the optical axis direction in the incident pupil of the objective lens or the vicinity thereof so that the light becomes parallel light.

With this type of total internal reflection microscope, it is preferable for the controller to identify the boundary of total reflection in the sample and non-total reflection in the sample based on the change in the intensity of the returning light.

With this type of total internal reflection microscope, the controller preferably calculates the incident angle of the light relative to the sample based on the amount of change of the incident angle adjustment part or the amount of change in the angle formed between the principal ray of the light and the optical axis of the relay optical system, which changes with the operation of the incident angle adjustment part.

With this type of total internal reflection microscope, the controller preferably calculates at least one of either the refractive index of the sample or the evanescent field penetration depth of based on the amount of change of the incident angle adjustment part, or the amount of change in the angle formed between the principal ray of the light and the optical axis of the relay optical system that changes with the operation of the incident angle adjustment part.

With this type of total internal reflection microscope, the controller preferably controls the incident angle adjustment part to obtain the desired evanescent field penetration depth.

With this type of total internal reflection microscope, the optical detector is preferably disposed in a position conjugate to the incident pupil plane or in the vicinity thereof.

With this type of total internal reflection microscope, the controller preferably determines a position of the image of the light source in the incident pupil plane based on the amount of change of the incident angle adjustment part, or the amount of change in the angle formed between the principal ray of the light and the optical axis of the relay optical system that changes with the operation of the incident angle adjustment part.

With this type of total internal reflection microscope, the controller preferably determines at least three or more of the positions on the boundary of total reflection and non-total reflection in the incident pupil plane, and determines the center of the circle that is the boundary from the positions.

With this type of total internal reflection microscope, the controller preferably detects the collecting state of the image of the light source relative to the incident pupil plane based on the change in intensity of the returning light when the position of the image of the light source is changed in the optical axis direction by the focus lens.

With this type of total internal reflection microscope, the incident angle adjustment part preferably is on the optical axis of the relay optical system, is disposed so as to intersect a position conjugate to the field of vision of the objective lens or in the vicinity thereof, has a reflective surface for reflecting the light, and changes the incident angle by changing the angle of the reflective surface relative to the optical axis with the point of intersection of the reflective surface with the optical axis as the center.

With this type of total internal reflection microscope, the incident angle adjustment part preferably changes the incident angle by changing the distance of the light source from the optical axis in the plane orthogonal to the optical axis.

With this type of total internal reflection microscope, the incident angle adjustment part preferably is on the optical axis of the relay optical system and changes the incident angle by rotating with a position conjugate to the field of vision of the objective lens or the vicinity thereof as the center.

Advantageous Effects of Invention

According to the present invention, the illumination angle of a total internal reflection microscope can be controlled with good precision with a simple configuration.

BRIEF DESCRIPTION OF DRAWINGS

FIG. 2A illustrates the change in intensity of the returning light in the area near the boundary, and FIG. 2B illustrates the position within the detection plane.

DESCRIPTION OF EMBODIMENTS

[First Embodiment]

Figure 1:
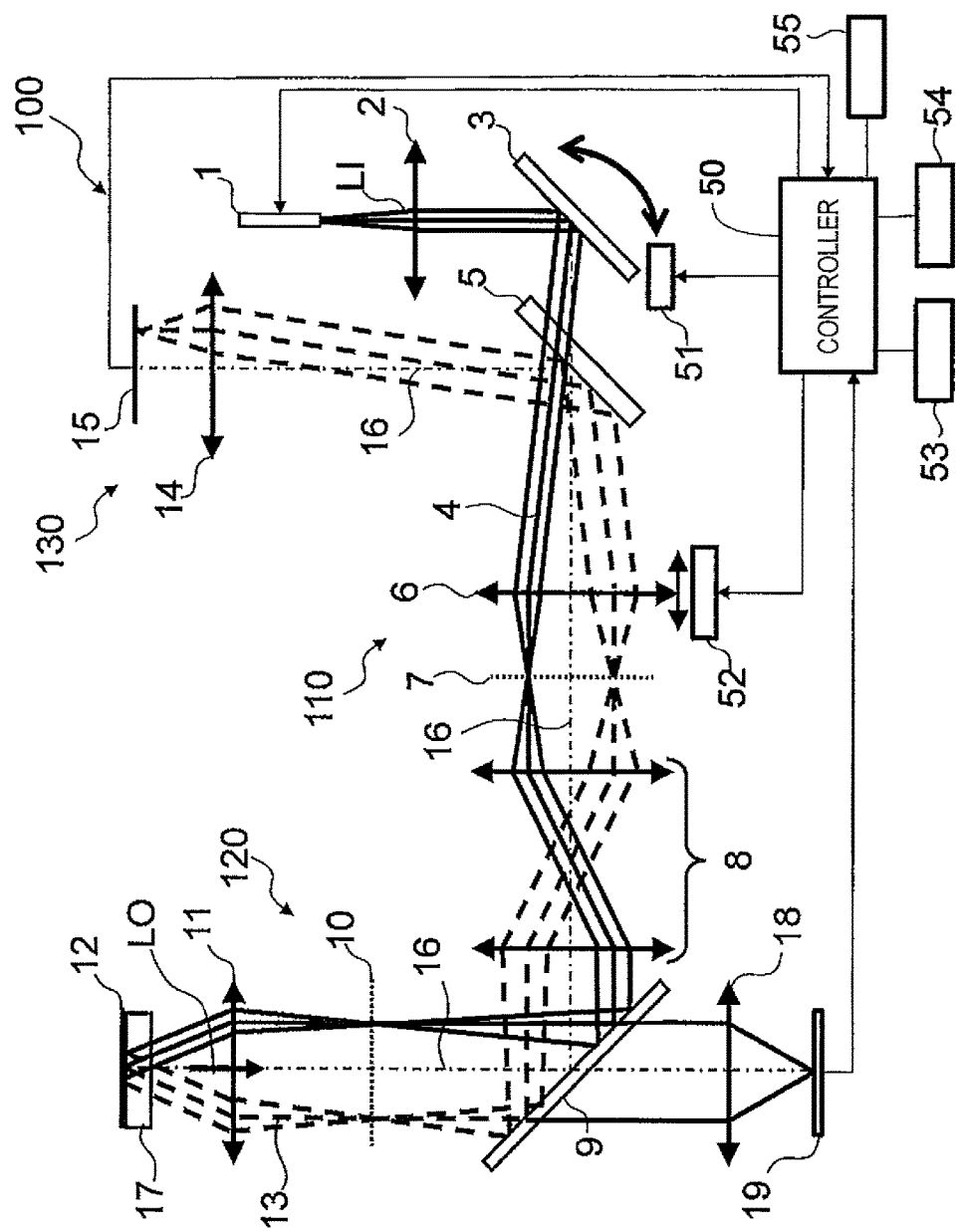
FIG. 1 is a descriptive drawing illustrating the configuration of the total internal reflection microscope according to the first embodiment.

A preferable embodiment of the present invention is described below with reference to the drawings. First, the configuration of a total internal reflection microscope 100 according to the first embodiment is described using FIG. 1. The total internal reflection microscope 100 is configured having an illumination optical system 110 for irradiating a sample 12 placed on a sample grounded glass 17 installed on a sample base, which is not pictured, by passing an illumination light LI emitted from a light source 1 through an objective lens 11 from the sample grounded glass 17 side, and an imaging optical system for collecting a fluorescence LO generated from the sample 12 which has been excited by the illumination light LI and collecting it onto the imaging plane of an imaging element 19 composed of a CCD or the like. Note that the light source 1 in FIG. 1 may be an end surface of an optical fiber directing illumination light emitted from a separate light source device to the illumination optical system 110. The objective lens 11 is a high NA objective lens that allows for total internal reflection microscope observation.

The illumination optical system 110 is configured from a collimating lens 2 for making the illumination light LI emitted from the light source 1 into substantially parallel light, an angle adjustment mirror 3 with high angular resolution that is an incident angle adjustment part for reflecting the illumination light LI emitted from the collimating lens 2 and adjusting the incident angle when the illuminated light LI irradiates the sample 12, a focus lens 6 for adjusting the parallelism of the illuminated light LI irradiating the sample 12, a relay lens 8 composed of at least two lenses for relaying the image of the light source 1, a first optical path splitter 9 configured as a dichroic mirror that reflects the illumination light LI toward the objective lens 11 and transmits the fluoresce LO generated from the sample 12 or a half-mirror (or half-prism) for transmitting one part of the light and reflecting the remaining light, and the sample 12 is disposed on the focal point on the object side of the objective lens 11. The reflective surface of the angle adjustment mirror 3 is displaced so as to intersect the field of vision of the objective lens 11 on the optical axis 16 at a substantially conjugate position (in the vicinity of a position conjugate to the field of vision), and the reflective surface of the angle adjustment mirror 3 is configured to rotate (oscillate) with a position conjugate the field of vision on the optical axis 16 or the vicinity thereof as the center. Note that the illumination light principal ray 4 is configured to be incident on the rotational center. The angle adjustment mirror 3 is configured to be rotatable in the X-axis direction and the Y-axis direction, where the optical axis 16 is the Z-axis and the orthogonal directions within a plane orthogonal to the optical axis 16 are each the X axis and Y axis. The light source 1 is disposed so as to substantially unite with the focal point of one of the collimating lenses 2. The symbol 10 of FIG. 1 illustrates the position of the emission pupil (pupil plane) of the objective lens 11, and the symbol 7 illustrates the conjugate position (pupil conjugate plane) of the pupil plane 10.

Also, the imaging optical system 120 is composed of, in order from the sample 12, the objective lens 11, the first optical path splitter 9, and an imaging lens 18, and the imaging plane of the imaging element 19 is disposed so as to substantially unite with the focal point plane on the image side of the imaging lens 18.

With this type of a total internal reflection microscope 100, the illumination light LI emitted from the light source 1 is made into substantially parallel light by the collimating lens 2 and reflected by the angle adjustment mirror 3. Then, after it is momentarily collected by the focus lens 6 at the pupil conjugate plane 7 of the objective lens 11 or the vicinity thereof and forms the image of the light source 1, it is relayed by the relay lens 8, reflected by the first optical path splitter 9, and is collected at the pupil plane 10 of the objective lens 11 or the vicinity thereof and reforms the image of the light source 1. Then, the illumination light LI is collimated by the objective lens 11, made into substantially parallel light, and irradiates the sample grounded glass 17. At this time, because the principal ray of the illumination light LI is reflected by the angle adjustment mirror 3 so as to form a predetermined angle relative to the optical axis, the image of the light source 1 is formed at a position apart from the optical axis 16 of the pupil plane 10 or the vicinity thereof, and the illumination light LI is irradiated diagonally, with a predetermined incident angle relative to the sample grounded glass 17. Here, the incident angle refers to the angle formed by the principal ray of the illumination light LI and the normal to the boundary plane of the sample 12 and the sample grounded glass 17 (a line substantially parallel to the optical axis 16). At this time, when the incident angle exceeds the critical angle of the boundary plane of the sample 12 and the sample grounded glass 17, the illumination light LI is totally reflected at the boundary plane. Light (evanescent light) permeates and forms an evanescent field on the side of the sample 12 at the boundary plane of the sample grounded glass 17 and the sample 12 where the illumination light LI is totally reflected, and a range of several tens to several hundred nm of the thickness of the side of the sample 12 is illuminated. The fluorescence LO is generated from the sample 12, which is excited by the evanescent light. When the focal point plane on the object side of the objective lens 11 is adjusted to be positioned at this position, the fluorescence LO is collected by the objective lens 11, made into substantially parallel light, passes through the first optical path splitter 9, and collected on the imaging plane of the imaging element 19 by the imaging lens 18; an image of the sample 12 is formed by the fluorescence LO. In this manner, a high-contrast image can be obtained by the total internal reflection microscope 100 because the sample 12 can be excited in an extremely dark state with little light noise in the background. Note that the position of the image of the light source 1 in the optical axis direction formed on the pupil conjugate plane 7 or the vicinity thereof is changed by moving the focus lens 6 in the optical axis direction, and as a result, the position of the image of the light source 1 formed on the pupil plane 10 or the vicinity thereof is changed. Thus, by uniting the image of the light source 1 with the pupil conjugate plane 7 via the focus lens 6, the image unites with the pupil plane 10, and this allows the illumination light LI irradiating the sample 12 via the objective lens 11 to be made parallel light (the parallelism can be adjusted). Also, the incident angle (the incident angle relative to the boundary plane) of the illumination light LI irradiating the sample 12 can be adjusted by changing the angle of the reflective surface of the angle adjustment mirror 3 relative to the optical axis 16.

With this type of the total internal reflection microscope 100, because the amount of evanescent light permeating the boundary plane is dependent on the incident angle of the illumination light LI incident on the boundary plane, the illumination light LI incident on the boundary plane must be made close to parallel light. Because of this, the total internal reflection microscope 100 is equipped with a returning light detector 130 for detecting the illuminated light having been totally reflected at the boundary plane of the sample grounded glass 17 and the sample 12 (this illuminated light is called "returning light" below), and along with distinguishing whether or not the illumination light LI was totally reflected at the boundary plane of the sample grounded glass 17 and the sample 12 with the returning light detector 130, it is configured to secure a state of total reflection illumination by the angle of the angle adjustment mirror 3 in the boundary state (critical state) of total reflection and non-total reflection.

The returning light detector 130 is composed of a second optical path splitter 5 disposed on the optical axis between the focus lens 6 and the angle adjustment mirror 3, a condensing lens 14 disposed on the side of the second optical path splitter 5, and an optical detector 15 disposed so one focal point plane of the condensing lens 14 is substantially united with the detection plane. Note that the second optical path splitter 5 is composed of a half mirror (or half prism) that transmits one part of the light and reflects the remaining light. The second optical path splitter 5 is disposed on the focal point plane on the image side of the objective lens 11 or the vicinity thereof, and on the side of the sample 12 from the angle adjustment mirror 3. Note that the symbol 13 in FIG. 1 illustrates the principal ray of the returning light.

The illumination light (returning light) that is totally reflected at the boundary plane of the sample grounded glass 17 and the sample 12 is reflected by the first optical path splitter 9 after being collected on the pupil plane 10 by the objective lens 11, and is further relayed by the relay lens 8 and the focus lens 6, and one part of the light is reflected by the second optical path splitter 5. Then, the returning light reflected by the second optical path splitter 5 is collected onto the detection plane of the optical detector 15 by the condensing lens 14. Here, because the detection plane of the optical detector 15 is disposed at a position conjugate to the pupil plane 10 of the object lens 11 or the vicinity thereof, it is possible to detect the collecting state (focus state) of the illumination light collected on the pupil plane 10 and the collecting position on the pupil plane 10, and when the state of the illumination light LI collected on the pupil plane 10 is changed by moving the focus lens 6 in the optical axis direction or the angle adjustment mirror 3 is swung (rotated or moved), it is possible to grasp the state thereof.

Further, concerning the returning light detector 130, it is possible to differentiate between the total reflection light (the illumination light LI having been totally reflected at the sample grounded glass 17 and the sample 12) and the reflected light reflected by the sample 12, which have an intensity ratio of approximately 100:4, by detecting the intensity of the returning light; it is possible to determine the boundary between total reflection and non-total reflection from the intensity of the light detected by the optical detector 15. Note that for this manner of the optical detector 15 of the returning light detector 15, it is desired that the CCD or position sensitive detector (PSD) and the like are able to detect the focus state and intensity of the light collected on the detection plane. Further, because the detection plane of the optical detector 15 is substantially conjugate to the pupil plane 10, it is possible to calculate the total reflection angle of the illuminated light LI incident on the sample 12, the refractive index of the sample 12, and the evanescent field penetration depth by detecting the collecting position on the detection plane; however, the precision thereof depends on the resolution of the detection element, and the precision is not very high.

Now, a method for adjusting the parallelism and incident angle of the illumination light LI irradiating the sample 12 by detecting the spot of the returning light via the optical detector 15 is described. Note that here, a description is given for a case wherein a CCD is used as the detector 15, as well a case wherein a position sensitive detector (PSD) is used.

(Case wherein a CCD is Used as the Detector 15)

First, an adjustment method for a case wherein a CCD is used as the detector 15 is described. When the focus lens 6 is moved in the optical axis direction, the spot diameter of the returning light collected on the optical detector 15 of the returning light detector 130 changes, and the peak intensity also changes. Specifically, when the image of the light source 1 unites with the pupil plane 10, the spot diameter detected by the optical detector 15 is minimized, and the peak intensity is maximized. That is, by adjusting the focus lens so that the spot diameter is minimized and the peak intensity is maximized, the image of the light source 1 is positioned on the pupil plane 10, and the illumination light irradiating the sample 12 becomes parallel light, and this causes the illumination angle calculation precision described next to increase.

A method for adjusting the incident angle of the illumination light LI onto the sample 12 via the angle adjustment mirror 3 is described next. Here, the relationship between the incident angle θ of the illumination light LI incident on the sample 12 and the position in the pupil plane 10 that the illumination light LI is collected can be found with the following expression (1).

[Equation 1]

$$\theta = \sin^{-1}\left(\frac{h}{n_1 f}\right) \quad (1)$$

In expression (1), h is the distance from the collecting position of the illumination light LI in the pupil plane 10 to the center of the pupil plane 10, that is, the optical axis 16; $n_1$ is the refractive index of the sample grounded glass 17; and f is the focal distance of the objective lens 11. Further, when the reference position (0°) is set to when the angle $\theta_m$ of the reflective surface of the angle adjustment mirror 3 is at 45° relative to the optical axis 16, the distance h is found by the next expression (2) from the angle $\theta_m$ and the combined focal distance f1 of the optical system from the angle adjustment mirror 3 to the pupil plane 10. Note that when the reflection angle of the angle adjustment mirror 3 is changed by an angle $\theta_m$, the light (the principal ray of the light) reflected by the reflective surface of the angle adjustment mirror 3 changes by an angle $2\theta_m$ relative to the optical axis.

[Equation 2]

$$h = f1 \sin 2\theta_m \quad (2)$$

Then, when the incident angle θ of the illumination light LI relative to the vector of the boundary plane between the sample grounded glass 17 and the sample 12 exceeds the angle $\theta_r$ illustrated in the following expression (3), the illumination light LI is totally reflected at the boundary plane, and total internal reflection microscope observation becomes possible.

[Equation 3]

$$\theta_r = \sin^{-1}\left(\frac{n_2}{n_1}\right) \quad (3)$$

Here, $n_1$ is the refractive index of the sample grounded glass 17, and $n_2$ is the refractive index of the sample 12. In general, it is often the case that an accurate value for the refractive index of the sample 12 is unknown and the angle of illumination light and the like must be found by hand when making adjustments for performing total internal reflection microscope observation, but the total internal reflection microscope 100 according to the present embodiment is configured so that this value can be calculated by the method shown below.

The relationship between the incident angle θ of the illumination light relative to the sample 12 and the depth of the evanescent field, that is, the depth range d (depth in the optical axis direction from the boundary plane) of the illumination light hitting the sample 12 is illustrated by the following expression (4). However, λ is the wavelength of the illumination light.

[Equation 4]

$$d = \frac{\lambda}{4\pi\sqrt{n_1^2 \sin^2\theta - n_2^2}} \quad (4)$$

As is clear from the expression (4), the incident angle θ of the illumination light LI should be adjusted in order to adjust the penetration depth d of the evanescent field; that is, the collecting position h of the illumination light LI in the pupil plane 10 should be adjusted with the angle adjustment mirror 3.

Figure 2A:
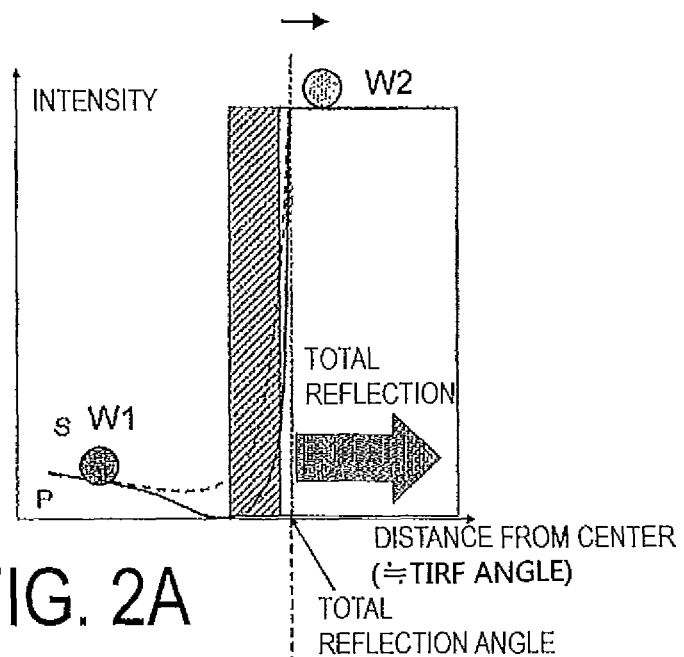
FIGS. 2A and 2B are descriptive drawings for describing the method of detecting the boundary of total reflection and non-total reflection, where
Figure 2B:
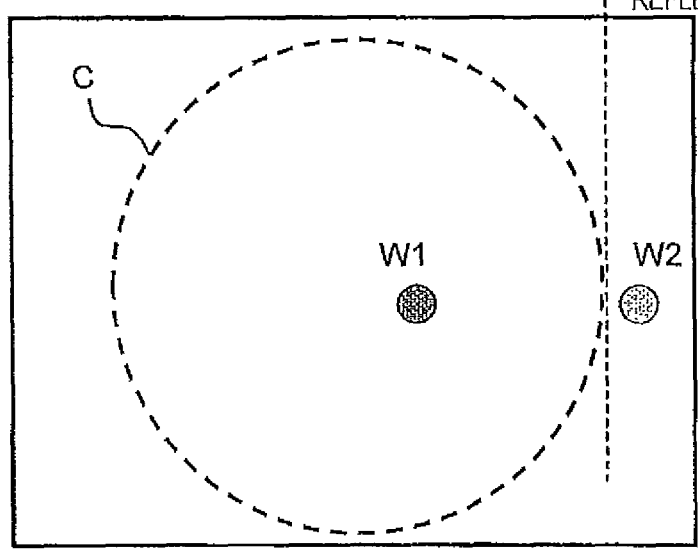
Figure 3:
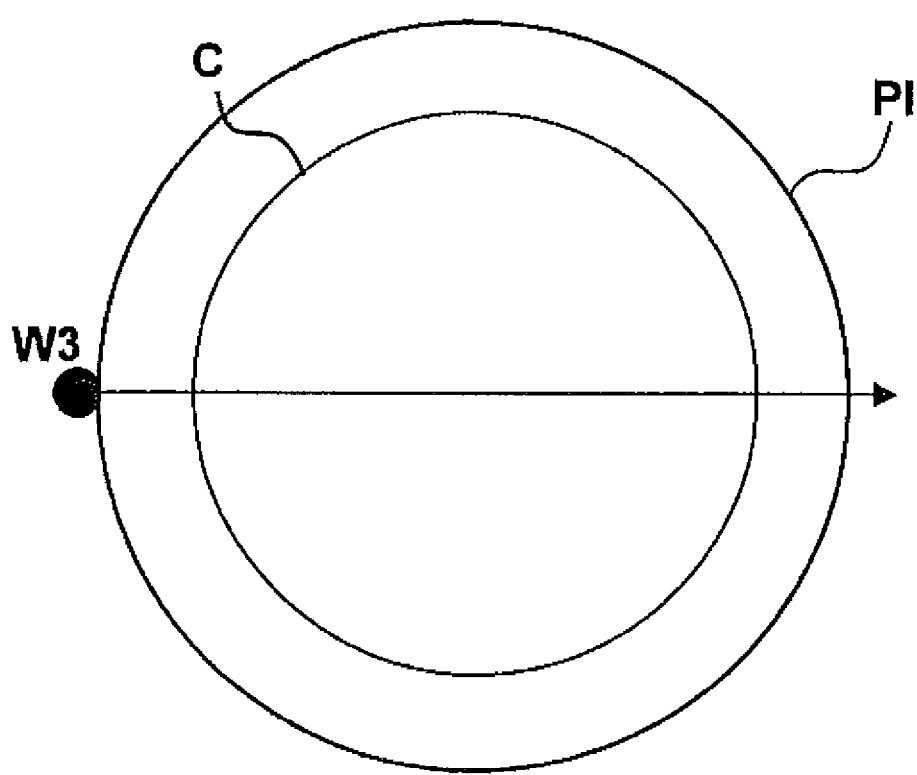
FIG. 3 is a descriptive drawing for describing the movement of the spot on the optical detector.
Figure 4:
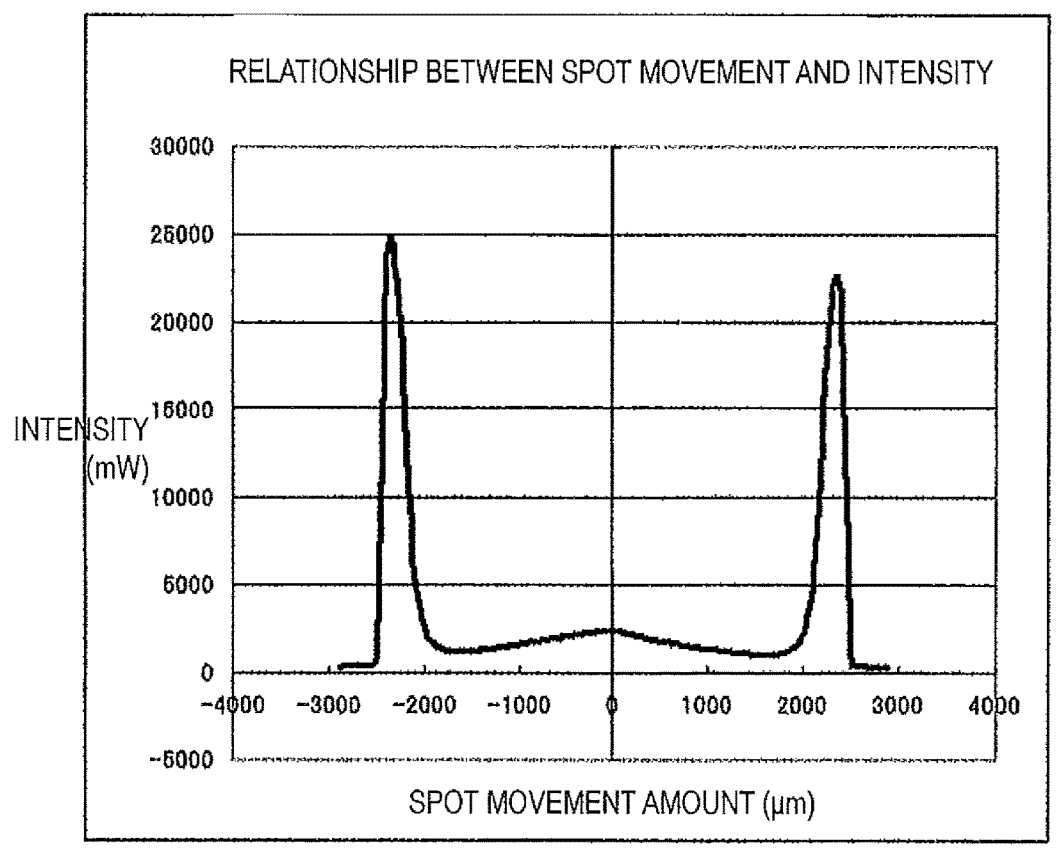
FIG. 4 is a descriptive drawing illustrating the change in intensity when moving the spot on the optical detector.

As described above, swinging the angle adjustment mirror 3 moves the position of the image of the light source 1 in the pupil plane 10, and this causes the spot position of the returning light collected on the optical detector 15 of the returning light detector 130 to move within the detection plane of the detector 15. At this time, in a detection plane conjugate to the pupil plane 10, when the center of the optical detector 15 is orthogonal to the optical axis, the spot intensity of the returning light changes significantly (FIG. 2A) between the inside and the outside of a predetermined circle (circle C in FIG. 2B) with the center thereof being the center of the detection plane. The spot intensity ratio of the inside and outside of the circle C is 4:100, and when the spot is inside the circle C, the illumination light LI is in a state such that it is incident below the total reflection angle at the sample 12, and when the spot is outside the circle C, the illumination light LI is in a state such that it is incident above the total reflection angle at the sample 12. That is, the circle C shows the boundary of total reflection and non-total reflection in the boundary plane of the sample grounded glass 17 and the sample 12, and by moving the spot of the returning light in the vicinity of the circle C in the detection plane of the detector 15 so that it intersects the circle C by changing the angle of the angle adjustment mirror 3 and detecting the position where the intensity thereof changes, it can be adjusted to a state wherein the illumination light LI is totally reflected at the boundary plane of the sample grounded glass 17 and the sample 12. Note that the radius of the circle C is dependent on the magnification of the objective lens 11, the refractive index of the sample 12, the wavelength of the illumination light LI, and the like, and while the circle may deform by the optical element, which is on the optical path, and the center of the circle may become offset from the center of the optical axis, by determining the angle of total reflection from the intensity of the returning light as described above, an adjustment with good precision can be performed. For example, in an observation using an objective lens with magnification 60× and NA 1.49, as illustrated in FIG. 3, circle PI in the detection plane of the optical detector 15 corresponds to the pupil diameter of the pupil plane 10, and when the spot W3 is moved so it crosses the circle C from the outside of the circle PI (along the arrow illustrated in FIG. 3), the relationship between the movement of the spot W3 and the detection intensity can be obtained as illustrated in FIG. 4. The portion with increased intensity is in a state of being totally reflected in the sample plane, and the total reflection boundary position can be detected therewith.

Figure 5:
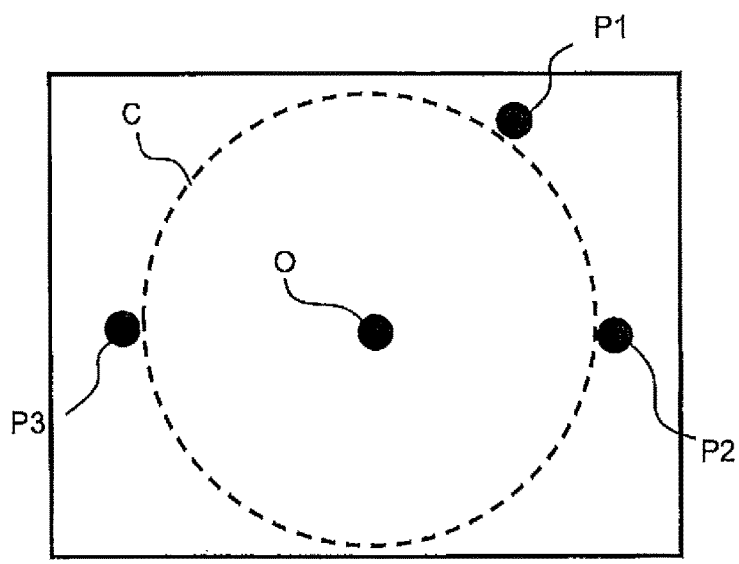
FIG. 5 is a descriptive drawing describing the relationship between the measurement point on the detection plane and the boundary of total reflection and non-total reflection.

When the spot is on the boundary or the outside of the circle C, the illumination light LI is in a state of being incident on the sample 12 at the critical angle for total reflection, and with the total internal reflection microscope 100, observation is generally performed in this vicinity. Note that while it is possible to perform total internal reflection microscope observation by detecting the angle of the angle adjustment mirror 3 that makes the incident angle of the illumination light LI incident on the boundary plane of the sample grounded glass 17 and the sample 12 become the critical angle for total reflection according to the method described above (can be converted to the angle formed by the light (principal ray of the light) reflected by the reflection plane of the angle adjustment mirror 3 and the optical axis), it is possible to calculate the total reflection angle $\theta_r$ of the illumination light LI incident on the sample 12 from the position of the spot based on the position (coordinates) and radius of the center of the circle C, and further, the calculate the refractive index $n_2$ of the sample 12 and evanescent field penetration depth d based on the expressions (3) and (4) described above. Specifically, as illustrated in FIG. 5, by performing detection of positions that is totally reflected at three or more places in the detection plane (for example, at points P1-P3 in FIG. 5), the coordinates of the center O of the circle C and the radius of the circle C can be found from each of these coordinates.

Here, the radius of the circle C can be detected accurately if the angular resolution of the angle adjustment mirror 3 is high, and the precision thereof depends on the intensity detection resolution of the optical detector 15, but does not depend on the position detection resolution. That is, a state of being in the boundary of total reflection (the circle C) is detected from the optical detector 15, and by calculating the position of the image of the light source 1 in the pupil plane 10 from the angle $\theta_m$ of the angle adjustment mirror 3, the radius of the circle C can be found with good precision. Generally, the intensity detection resolution of a CCD or position sensitive detector (PSD) and the like has 256 gradations or more, and is sufficiently high for discerning reflection from total reflection and has little impact on cost.

According to the above procedure, managing the incident angle of the illumination light LI relative to the sample 12 in the total internal reflection microscope 100, that is, the evanescent field penetration depth can be performed with high precision and low cost.

Figure 6:
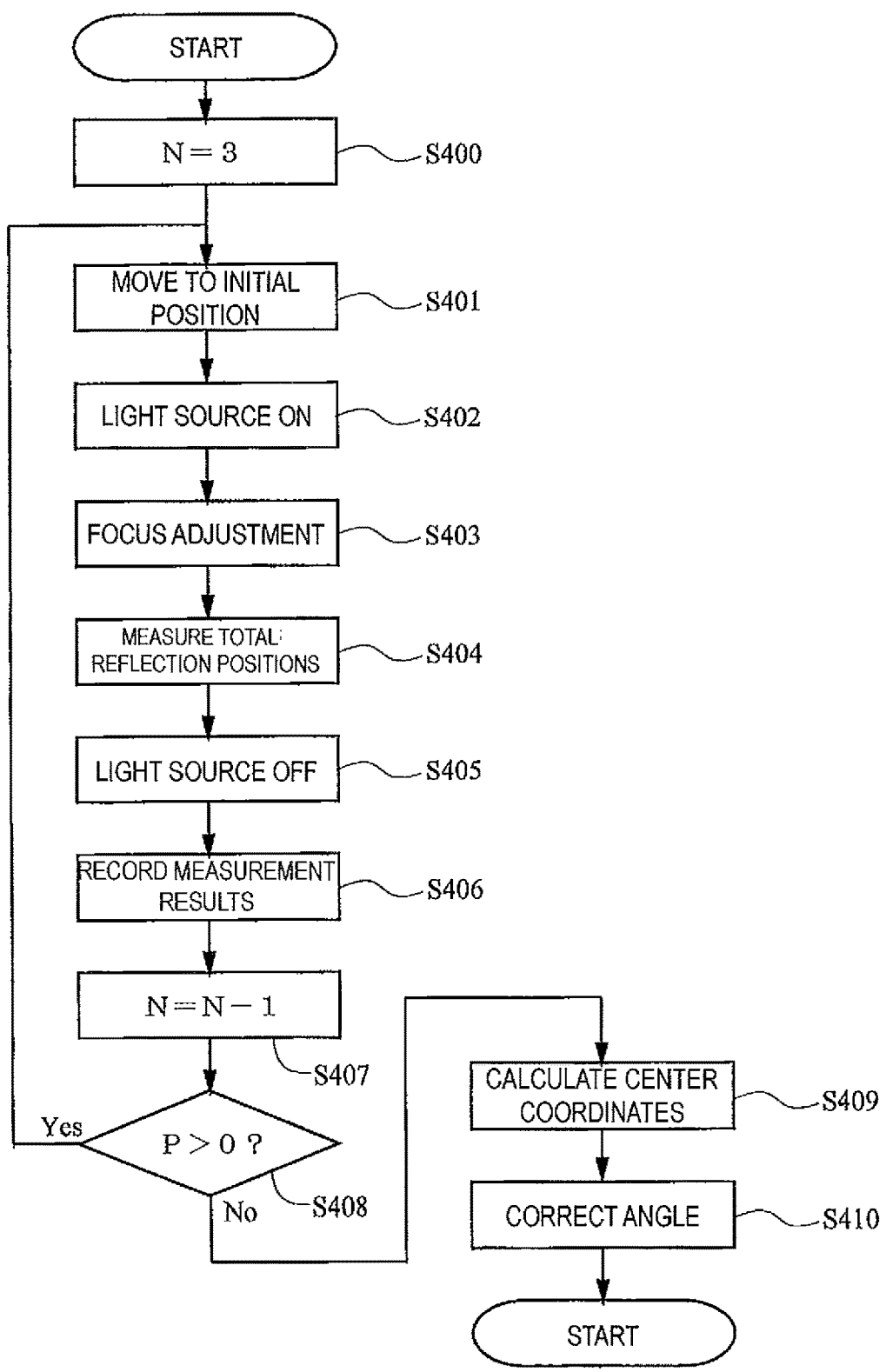
FIG. 6 is a flow chart of the adjustment method of total reflection illumination performed by detecting the boundary of total reflection and non-total reflection.

Note that as illustrated in FIG. 1, the parallelism and incident angle of the illumination light LI irradiating the sample 12 can be controlled by providing an angle adjustment actuator 51 for rotating the angle adjustment mirror 3 and a position adjustment actuator 52 for moving the focus lens 6 in the optical axis direction and a controller 50 for controlling the operations thereof and controlling the actuators 51 and 52 based on the detection results (spot intensity of the returning light) from the optical detector 15 from the controller 50. Also, an input part 53 for the observer to operate, a memory part 54 for recording information for adjusting the total reflection illumination and images of the sample 12 obtained by the imaging element 19, and a display part 55 for displaying and the like of settings information and obtained images are connected to the controller 50. Then, the adjustment process of the total reflection illumination by the controller 50 is described using FIG. 6. Note that here, a case where positions of total reflection are measured at three points in the detection plane of the optical detector 15 and adjusted is described.

The controller 50 sets the number N of places to measure for adjusting when the start of adjustment processes of total reflection illumination are indicated (step S400). This number N of measurement places may be recorded beforehand in the memory part 53 or input by the observer from the input part 53 (here, N is set to 3 as described above). Then, the controller 50 first sets the angle of the angle adjustment mirror 3 by operating the angle adjustment actuator 51 so that the image of the light source 1 is formed on the initial position for performing measurements on the pupil plane 10, which is the first point (step S401). Note that because the critical angle at which the illumination light LI is totally reflected at the boundary plane of the sample grounded glass 17 and the sample 12 is determined by the focal length and the like of the objective lens 11, the initial position at which measurement is started may be recorded beforehand in the memory part 54 for each type of objective lens 11. The angle of the angle adjustment mirror 3 relative to the optical axis 16 may be found from the operation amount of the angle adjustment actuator 51, or by providing an angle detector separate from the actuator 51 that is configured to detect. The position of the focus lens 6 is the same manner. Also, here, as illustrated in FIG. 2, a case wherein it is configured with a point inside the circle C showing the boundary (critical angle) of total reflection and non-total reflection (point W1 of FIG. 2B) as the initial point is described.

Next, the controller 50 turns on the light source 1 and emits illumination light (step S402) and operates the position adjustment actuator 52 and moves the focus lens 6 in the optical axis direction, moving it to a position such that the spot diameter detected by the optical detector 15 is minimized and the peak intensity is maximized (step S403). This increases the parallelism of the illumination light LI at the current measurement position relative to the sample 12 (at the sample 12, the illumination light LI becomes substantially parallel light). The controller 50 operates the angle adjustment actuator 51 and rotates the angle adjustment mirror 3, moves the image of the light source 1 in the pupil plane 10 in the direction away from the optical axis 16, and as illustrated in FIG. 2A, stops the angle adjustment mirror 3 at a position (point W2 of FIG. 2B) at which the spot intensity detected by the optical detector 15 is higher than at the initial position (step S404), and turns off the light source 1 (step S405). The controller 50 determines the current position (coordinates in the pupil plane 10) of the image of the light source 1 from the angle of the angle adjustment mirror 3 and records it in the memory part 54 (step S406), subtracts 1 from the number N of measurement places (step S407), determines whether the number N of measurement places is larger than 0 and repeats the processes S401 through S407 until the number N of measurement places becomes 0 (step S408). Finally, the controller 50 finds the center coordinates and radius of the circle C at the critical angle from the coordinates (angle of the angle adjustment mirror 3) of the three places measured as described above (step S409), and from the center coordinates and radius of the circle C, the angle $\theta_m$ of the angle adjustment mirror 3 to provide the evanescent field penetration depth d desired by the observer is determined and set by the angle adjustment actuator 51 (step S410), and the adjustment processes of total reflection illumination are finished. Note that in step S409, it may be configured to calculate the refractive index $n_2$ of the sample 12.

If configured as described above, the focus adjustment via the focus lens 6 (process for uniting the image of the light source 1 with the pupil plane 10) and the adjustment of the angle adjustment mirror 3 to obtain the desired evanescent field penetration depth d can be performed automatically by the control of the controller 50. At this time, as described above, it is sufficient for the optical detector 15 to be able to detect the intensity of the returning light, and does not need to be able to identify the position of the spot on the detection plane.

(Case wherein a PSD is Used as the Optical Detector 15)

Figure 7:
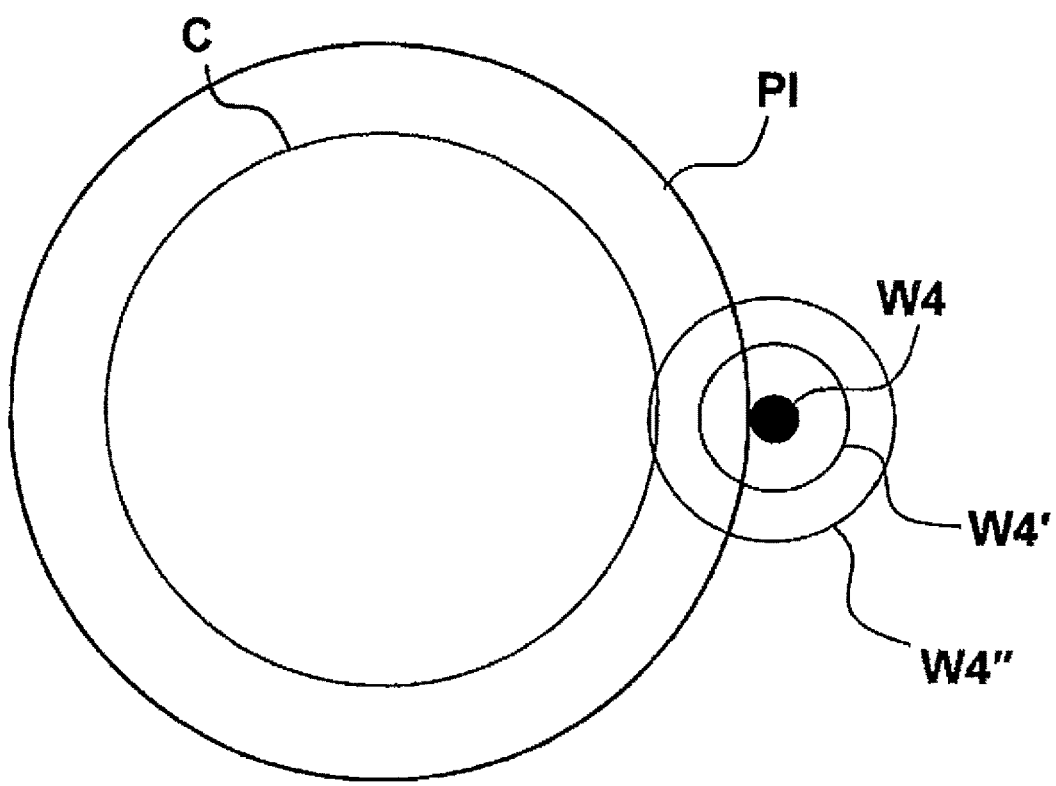
FIG. 7 is a descriptive drawing for describing the state of the spot when operating the focus adjustment lens.
Figure 8:
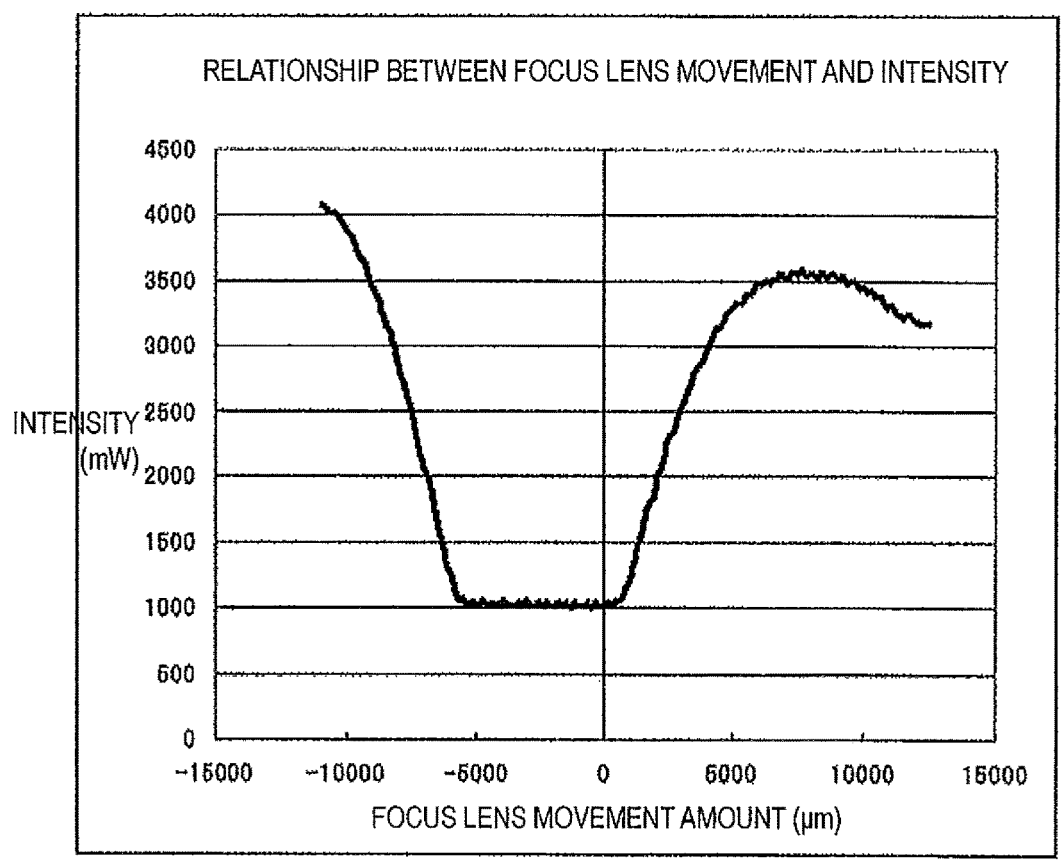
FIG. 8 is a descriptive drawing illustrating the change in intensity when operating the focus adjustment lens.

A method for adjusting focus in a case wherein a PSD is used as the optical detector 15 is described next. Before adjusting the focus lens 6, the angle adjustment mirror 3 is swung and the spot position of the returning light on the optical detector 15 is moved. The optical detector 15 is conjugate to the pupil plane 10, and as illustrated in FIG. 7, the circle PI in the detection plane of the optical detector 15 corresponds to the pupil diameter of the pupil plane 10, and when the spot W4 is moved to the outside of the circle PI, the returning light no longer reaches the optical detector 15. When the focus lens 6 is moved in the optical axis direction when in a state where the spot W4 is just outside the circle PI, at the point where the position of the image of the light source 1 is about to go outside the pupil plane 10, the spot diameter of the returning light becomes larger as in W4' and W4" of FIG. 7, and because the returning light juts out into the circle PI, the returning light becomes detectable. FIG. 8 shows the change in intensity when the focus adjustment lens 6 is moved with the spot W4 of the returning light in the outer vicinity of the circle PI, when observing using an objective lens with magnification 60× NA 1.49. When the position of the image of the light source 1 is removed from the pupil plane 10 in the optical axis direction (a position in front of or behind the pupil plane in the optical axis direction), the returning light is detected by the optical detector 15, so the focus lens 6 is moved in the optical axis direction, and by making the center of the movement range (focus range) of the focus adjustment lens 6 where the returning light is not detected the optimal position, that is, by making it the position where the image of the light source 1 is formed on the pupil plane 10, the illumination light irradiating the sample 12 becomes parallel, and this improves the illumination angle detection precision described next.

Note that the method for adjusting the incident angle of the illumination light LI to the sample 12 via the angle adjustment mirror 3 is the same as in the case described above where a CCD is used as the optical detector 15.

[Second Embodiment]

Figure 9:
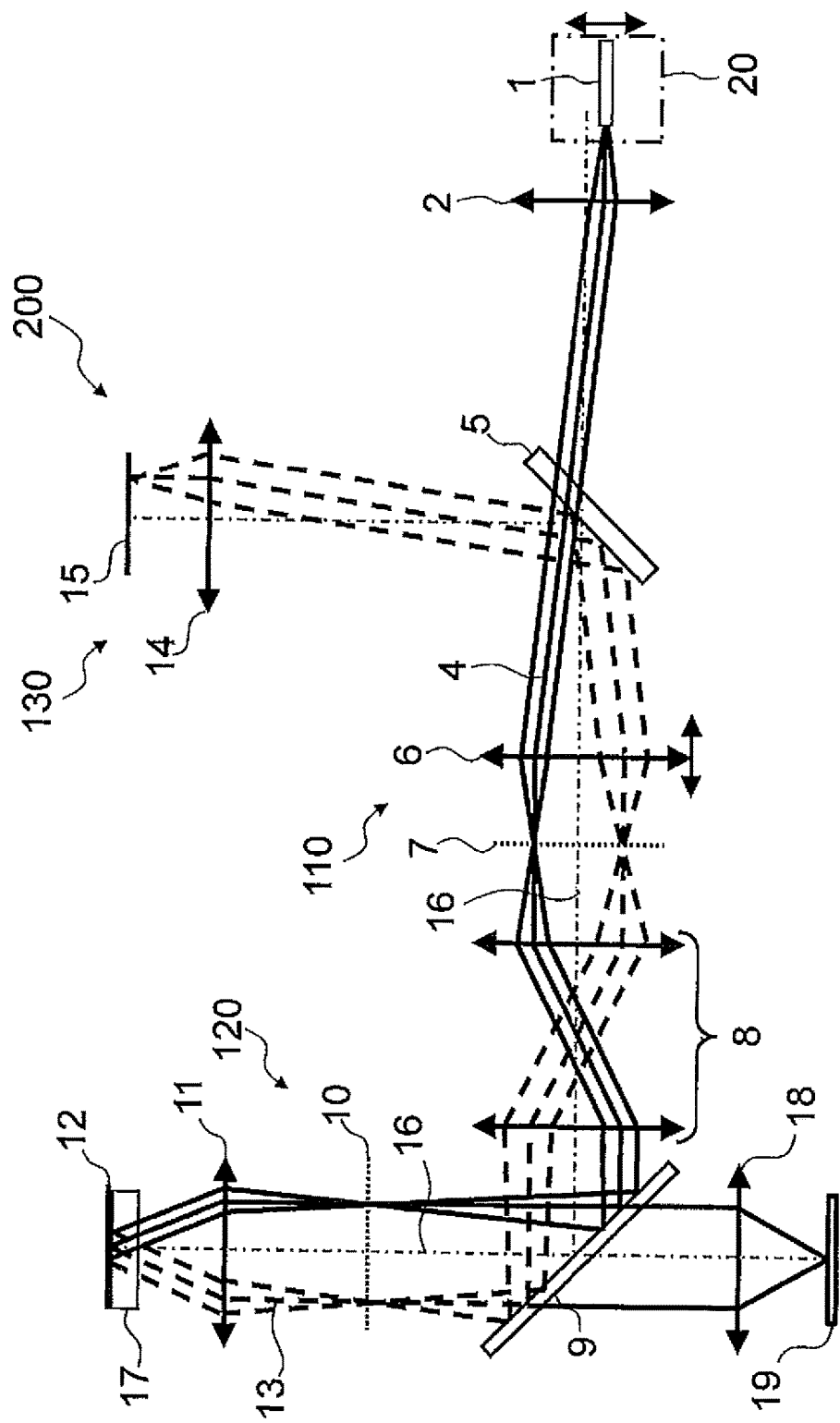
FIG. 9 is a descriptive drawing illustrating the configuration of the total internal reflection microscope according to the second embodiment.
Figure 10:
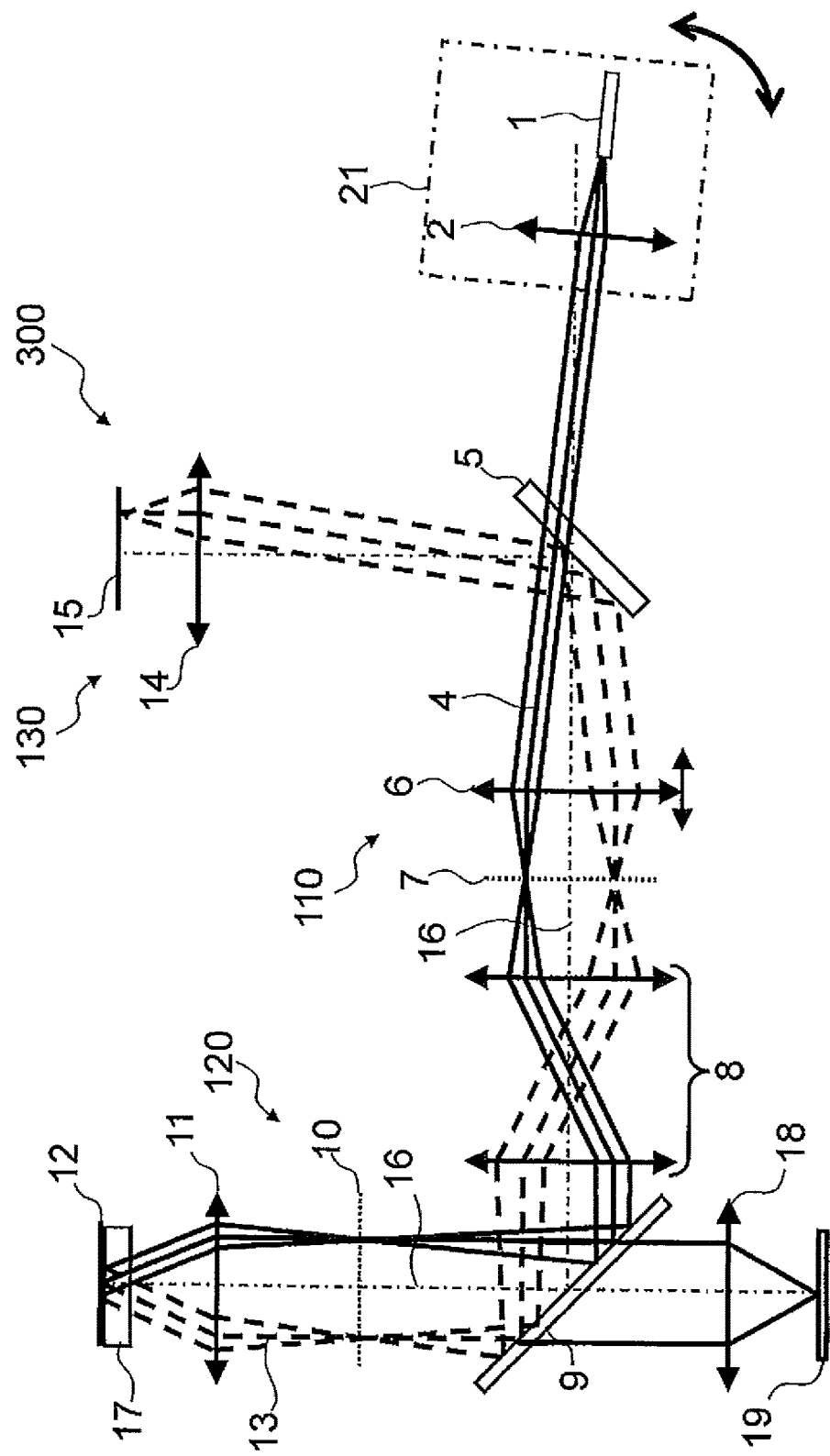
FIG. 10 is a descriptive drawing illustrating the configuration of the total internal reflection microscope according to the third embodiment.

The total internal reflection microscope 100 according to the first embodiment is configured to have the illumination light LI is totally reflected at the boundary plane of the sample grounded glass 17 and the sample 12 by controlling the angle of the angle adjustment mirror 3 that reflects the illumination light LI from the light source 1, but the total internal reflection microscope 200 according to the second embodiment describes a configuration that moves the light source 1 in the direction orthogonal to the optical axis 16 as illustrated in FIG. 9, and by emitting a principal ray 4 of the illuminated light LI emitted from the light source so it is parallel to the optical axis, adjusts the position of the image of the light source 1 in the pupil plane 10. Note that constituent members that are the same as in the total internal reflection microscope 100 according to the first embodiment are given the same symbols, and the descriptions thereof are omitted.

The principal ray of the illumination light LI emitted from the light source 1 proceeds parallel to the optical axis 16, and is converted to substantially parallel light by the collimating lens 2. At this time, the light source 1 is held by a light source holding part 20 and is configured to move the light source 1 in a direction substantially orthogonal to the optical axis 16 while maintaining the emission direction of the illumination light from the light source 1. The angle formed between the substantially parallel light emitted from the collimating lens 2 and the optical axis 16 is determined according to the distance from the optical axis 16 of the light source 1. The substantially parallel light is transmitted through the second optical path splitter 5, collected to a pupil conjugate plane 7 of the objective lens 11 by the focus lens 6 or the vicinity thereof, further relayed by the relay lens 8, reflected by the first optical path splitter 9 and forms an image of the light source 1 on the pupil plane of the objective lens 11 or the vicinity thereof, is made into substantially parallel light by the objective lens 11, and irradiates the boundary plane of the sample grounded glass 17 and the sample 12 at a predetermined angle. Note that the focus adjustment via the focus lens 6 (process for uniting the image of the light source 1 with the pupil plane 10) is the same as in the first embodiment. In FIG. 9, the configuration of the controller 50 and the like are omitted.

In the total internal reflection microscope 200 according to the second embodiment, the collecting position (position of the image of the light source 1) of the illumination light LI in the pupil plane 10, that is, the incident angle θ of the illumination light LI incident on the sample 12 is performed by moving the light source 1 in a direction orthogonal to the optical axis, as described above. That is, the light source holding part 20 that moves the light source 1 in the optical axis direction functions as the incident angle adjustment part. Here, the distance h of the collecting position (position of the image of the light source 1) of the illumination light LI in the pupil plane 10 and the optical axis 16 (center of the emission pupil of the objective lens 11) is found by the following expression (2'). Note that in this expression (2'), p is the projection magnification of the light source 1 onto the pupil plane 10, and $h_0$ is the distance between the light source 1 and the optical axis 16.

[Equation 5]

$$h = \beta h_0 \quad (2')$$

Even in the total internal reflection microscope 200 according to the second embodiment, even if the intensity detection resolution of the optical detector 15 is low, as long as the resolution for determining the position from the optical axis 16 of the light source 1 of the light source holding part 20 is high, the incident angle of the illumination light LI relative to the sample 12 in the total internal reflection microscope 200, that is, management of the evanescent field penetration depth can be performed with high precision and low cost.

[Third Embodiment]

The total internal reflection microscope 300 according to the third embodiment illustrates a configuration wherein the light source 1 and the collimating lens 2 rotate (swing) as one body, in place of the configuration in the total internal reflection microscope 100 according to the first embodiment where the angle of the illumination light LI relative to the optical axis 16 was changed via the angle adjustment mirror 3. Specifically, the total internal reflection microscope 300 is configured so a light source holding part 21 holds the light source 1 and the collimating lens 2 as one body and the principal ray 4 of the illumination light LI emitted from the light source 1 and made into substantially parallel light by the collimating lens 2 passes through a position conjugate to the field of vision on the optical axis 16, and the light source holding part 21 rotates (swings) with the position conjugate to the field of vision or the vicinity thereof as the center. That is, the light source holding part 21 functions as the incident angle adjustment part. The rest of the configuration is the same as in the first embodiment. Also for the total internal reflection microscope 300 according to the third embodiment if the resolution of the rotation amount of the light source holding part 21 is high, the management of the incident angle of the illumination light LI relative to the sample 12, that is the evanescent field penetration depth in the total internal reflection microscope 300 can be performed with high precision and low cost.

Note that in each embodiment described above, it is preferable for the "vicinity of the pupil plane 10 of the objective lens 11" to be a position within a range of 5 mm from the pupil plane 10.

Also, regarding the "vicinity of the position conjugate to the pupil plane 10 of the objective lens 11" in each embodiment described above, it is set based on the magnification of the position conjugate to the pupil plane 10 of the objective lens 11. Specifically, the relay lens 8, the focus lens 6, and the condenser lens 14 relate to the setting of the magnification, and if the magnification determined by these three lenses is $\beta_a$ and the vicinity of the pupil plane 10 is 6, the vicinity of the conjugate position $\Delta_a$ is $\Delta_a = \delta \times \beta_a^2$. For example, if $\delta = 5$ mm and $\beta_a = 0.5$, $\Delta_a = 5 \times 0.5^2 = 1.25$ mm, so the range becomes 1.25 mm.

To describe the method for setting the "vicinity of the position conjugate to the field of vision of the objective lens 11 on the optical axis 16", first, the focal depth degree is normally assumed to be the field of vision position of the objective lens 11, that is, the focus position. The focal depth $\Delta z$ is illustrated by the expression $\Delta z = n \times \lambda / (2 \times NA^2)$. n is the refractive index of the medium between the sample and the objective lens. $\lambda$ is the wavelength of the light from the light source 1, and NA is the NA of the objective lens 11. Then, the vicinity of a position conjugate to the field of vision position is set based on the magnification determined by the three lenses of the objective lens 11, the relay lens 8, and the focus lens 6. Then, if the magnification determined by these three lenses is $\beta_b$, the vicinity position $\Delta_b$ becomes $\Delta_b = \Delta z \times \beta_b^2$. For example, with an objective lens of NA 1.49, refractive index of the medium 1.52, and wavelength of the light from the light source 1 is $\lambda = 480$ nm (blue color), $\Delta z = 0.16$ μm. Then, if $\beta_b = 100$, the vicinity position $\Delta_b$ becomes $\Delta_b = \Delta z \times \beta_1 2 = 0.16 \times 100^2 = 1.6$ mm, so the range becomes 1.6 mm.

[Other]

Note that the requirements for each embodiment described above can be combined as suitable. Also, some constituent elements may not be used. Also, within the bounds permitted by law, the disclosure of all Japanese Patent Applications and U.S. Patents relating to the device quoted in each embodiment and modification described above are claimed as one part of the description given herein.

REFERENCE SIGNS LIST

1 Light source
3 Angle adjustment mirror (incident angle adjustment part)
6 Focus lens
8 Relay optical system
10 Objective lens incident pupil plane (pupil plane)
11 Objective lens
12 Sample
15 Optical detector
20, 21 Light source holding part (incident angle adjustment part)
50 Controller
100 Total internal reflection microscope
110 Illumination optical system
200, 300 Total internal reflection microscope

The invention claimed is:

1. A total internal reflection microscope comprising an illumination optical system for relaying light from a light source with a relay optical system and forming an image of the light source on the incident pupil of an objective lens or the vicinity thereof and irradiating an observation object with the light through the objective lens, the total internal reflection microscope further comprising:
   an incident angle adjustment device for changing the position of the image of the light source in a direction orthogonal to a direction of the optical axis,
   an optical detector for detecting intensity of the returning light that is the light reflected by the observation object and collected by the objective lens, and
   a controller for determining the operation amount of the incident angle adjustment device, wherein
   the controller determines the operation amount of the incident angle adjustment device based on the change in intensity of the returning light detected by the optical detector when the incident angle adjustment device is operated.

2. The total internal reflection microscope according to claim 1, further comprising
   a focus lens for changing the position of the image of the light source in the direction of the optical axis, wherein
   the controller determines the operation amount of the incident angle adjustment device and the focus lens based on the change in intensity of the returning light when the incident angle adjustment device and the focus lens are operated.

3. The total internal reflection microscope according to claim 2, wherein
the controller determines the operation amount of the incident angle adjustment device so the light is totally reflected at the sample based on the change in intensity of the returning light when the incident angle adjustment device is operated, and determines the operation amount of the focus lens so the light becomes parallel light based on the change in intensity of the returning light when the focus lens is operated.

4. The total internal reflection microscope according to claim 2, wherein
the controller adjusts the position of the light source image in the direction orthogonal to the direction of the optical axis in the incident pupil of the objective lens or the vicinity thereof so that the light is totally reflected at the observation object, and adjusts the position of the light source image in the direction of the optical axis in the incident pupil of the objective lens or the vicinity thereof so that the light becomes parallel light.

5. The total internal reflection microscope according to claim 2, wherein
the controller detects the collecting state of the image of the light source relative to the incident pupil plane based on the change in intensity of the returning light when the position of the image of the light source is changed in the direction of the optical axis by the focus lens.

6. The total internal reflection microscope according to claim 2, wherein
the controller determines the operation amount of the focus lens so the light becomes parallel light based on the change in intensity of the returning light when the focus lens is operated.

7. The total internal reflection microscope according to claim 2, wherein
the controller adjusts the position of the light source image in the direction of the optical axis in the incident pupil of the objective lens or the vicinity thereof so that the light becomes parallel light.

8. The total internal reflection microscope according to claim 1, wherein
the controller identifies the boundary of total reflection in the observation object and non-total reflection in the observation object based on the change in intensity of the returning light.

9. The total internal reflection microscope according to claim 1, wherein
the controller calculates the incident angle of the light relative to the observation object based on the operation amount of the incident angle adjustment device or the amount of change in the angle formed between the principal ray of the light and the optical axis of the relay optical system, which changes with the operation of the incident angle adjustment device.

10. The total internal reflection microscope according to claim 1, wherein
the controller calculates at least one of either the refractive index of the observation object or the evanescent field penetration depth based on the operation amount of the incident angle adjustment device, or the amount of change in the angle formed between the principal ray of the light and the optical axis of the relay optical system that changes with the operation of the incident angle adjustment device.

11. The total internal reflection microscope according to claim 1, wherein
the controller controls the incident angle adjustment device to obtain the desired evanescent field penetration depth.

12. The total internal reflection microscope according to claim 1, wherein
the optical detector is disposed in a position conjugate to the incident pupil plane or the vicinity thereof.

13. The total internal reflection microscope according to claim 1, wherein
the controller determines a position of the image of the light source in the incident pupil plane based on the operation amount of the incident angle adjustment device, or the amount of change in the angle formed between the principal ray of the light and the optical axis of the relay optical system that changes with the operation of the incident angle adjustment device.

14. The total internal reflection microscope according to claim 1, wherein
the controller determines three or more of the positions of the image of the light source in the incident pupil plane based on the change in intensity of the returning light, and determines the center of a circle corresponding to the boundary of total reflection and non-total reflection from the determined positions.

15. The total internal reflection microscope according to claim 1, wherein
the incident angle adjustment device is on the optical axis of the relay optical system, is disposed so as to intersect a position conjugate to the field of vision of the objective lens or the vicinity thereof, has a reflective surface for reflecting the light, and changes the incident angle by changing the angle of the reflective surface relative to the optical axis with the point of intersection of the reflective surface with the optical axis as the center.

16. The total internal reflection microscope according to claim 1, wherein
the incident angle adjustment device changes the incident angle by changing the distance of the light source from the optical axis in the plane orthogonal to the optical axis.

17. The total internal reflection microscope according to claim 1, wherein
the incident angle adjustment device is on the optical axis of the relay optical system and changes the incident angle by rotating with a position conjugate to the field of vision of the objective lens or the vicinity thereof as the center.

18. The total internal reflection microscope according to claim 1, wherein
the controller determines the operation amount of the incident angle adjustment device so the light is totally reflected at the observation object based on the change in intensity of the returning light when the incident angle adjustment device is operated.

19. The total internal reflection microscope according to claim 1, wherein
the controller adjusts the position of the light source image in the direction orthogonal to the direction of the optical axis in the incident pupil of the objective lens or the vicinity thereof so that the light is totally reflected at the observation object.

20. The total internal reflection microscope according to claim 1, wherein
   the observation object includes a sample, a holder that holds the sample, and a boundary between the sample and the holder.

21. The total internal reflection microscope according to claim 20, wherein
   the holder is a glass member that holds the sample.

* * * * *